(12) United States Patent
Edlund (10) Patent No.: US 10,913,937 B2
(45) Date of Patent: Feb. 9, 2021

(54) DEGRADATION OF SPOROPOLLENIN

(71) Applicant: LAFAYETTE COLLEGE, Easton, PA (US)

(72) Inventor: Anna F. Edlund, Easton, PA (US)

(73) Assignee: Lafayette College, Easton, PA (US)

( * ) Notice: Subject to any disclaimer, the term of this patent is extended or adjusted under 35 U.S.C. 154(b) by 0 days.

(21) Appl. No.: 15/955,416

(22) Filed: Apr. 17, 2018

(65) Prior Publication Data

US 2018/0298351 A1 Oct. 18, 2018

Related U.S. Application Data

(60) Provisional application No. 62/486,274, filed on Apr. 17, 2017.

(51) Int. Cl.
| | |
|---|---|
| *C12P 7/64* | (2006.01) |
| *C12N 9/08* | (2006.01) |
| *C09D 5/08* | (2006.01) |
| *C09D 5/00* | (2006.01) |
| *C09D 199/00* | (2006.01) |

(52) U.S. Cl.
CPC .............. *C12N 9/0065* (2013.01); *C09D 5/00* (2013.01); *C09D 5/008* (2013.01); *C09D 5/08* (2013.01); *C09D 199/00* (2013.01); *C12Y 111/01006* (2013.01); *C12Y 111/01007* (2013.01)

(58) Field of Classification Search
CPC . C09D 5/00; C09D 5/08; C09D 5/008; C12N 9/0065; C12Y 111/01007; C12Y 111/01006
USPC ................ 435/25, 419, 74; 424/70.11, 78.03
See application file for complete search history.

(56) References Cited

FOREIGN PATENT DOCUMENTS

WO WO2005000280 * 1/2005

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Sorensen et al. J. Coat tech. 2009, 6 pp. 135-166.*

* cited by examiner

*Primary Examiner* — Robert B Mondesi
*Assistant Examiner* — Mohammad Y Meah
(74) *Attorney, Agent, or Firm* — Vos-IP, LLC (57) ABSTRACT

A composition comprised of a perodixase, a catalase and a peroxide that, in combination, is suitable for degradation of pollen wall sporopollenin, and coatings comprising sporopollenin in a matrix that can be selectively degraded through application of a peroxidase, a catalase and a peroxide to the sporopollenin matrix.

12 Claims, 6 Drawing Sheets

FIG. 6C ns, or mixtures thereof. Sufficient quantities of sporopollenin are between 0.01% and 99% of the total weight of the composition. In a particularly preferred embodiment, the sporopollenin comprises between 1.0% and 50% of the total weight of the composition.
DEGRADATION OF SPOROPOLLENIN

PRIORITY CLAIM

This application claims priority to U.S. Provisional Patent Application No. 62/486,274, filed Apr. 17, 2017, which is hereby incorporated by reference in its entirety.

GOVERNMENT FUNDING

This invention was made with govern n support under Grant RUI#0744943 to A. F. E awarded by the National Science Foundation. The government has certain rights in the invention.

FIELD OF INVENTION

The present application is related to compositions and methods for degradation of sporopollenin, for coatings utilizing sporopollenin byproducts, and for generating materials having a non-toxic and inert coating thereupon.

BACKGROUND OF INVENTION

Most of the pollen grain walls ever made on earth are still here in layers of sediment. These sporopollenin walls are durable enough to withstand degradation by time, fungus, insect guts, and even treatment with concentrated sulfuric or hydrofluoric acids (Erdtman, 1960). Sporopollenin's chemical resistance makes it both worthy of, and difficult to, study. After one hundred years, its biochemical composition has yet to be revealed by extraction (Southworth, 1974), tracers, or solid-state methods (Dominguez, et al., 1999). To escape such durable walls after pollination, the delicate cells inside are believed to aim through the aperture closest to the stigma (Wolters-Arts et al., 1998). But apertures are not the only way out; many pollen grains are inaperturate (Furness, 2007), and in some flowers of the Brassicaceae family, including *Arabidopsis thaliana*, the pollen tube can breech inter-aperture exine for direct access to the stigma, regardless of the positions of the grain's three large apertures (Edlund et al., 2004; Hoedemaekers et al., 2015; Edlund et al., 2016).

The utility of sporopollenin is recognized for cosmetic and non-industrial uses. For example, U.S. Pat. No. 5,013,552, and DE 1990/2724 each describe the use of sporopollenin shells. Sporopollenin has also been described for carrying pharmaceutical cargo, e.g. WO 2007/0123856, and for other cosmetic uses in De 10221212.

Companies have formulated coatings with additives aimed at protecting against long term exposure to the elements. For example, WO 2010/064274 adds certain nanoparticles to various coatings to protect against corrosion. Chitin has also been used in certain coatings, for example in WP 1998/051711.

SUMMARY OF INVENTION

The present disclosure identifies a set of chemicals that, when combined together, degrade the otherwise ever-lasting substance sporopollenin. Making use of this degradation method, will allow identification and characterization of sporopollenin's composition and its eventual manufacture. Furthermore, the ability to selectively degrade sporopollenin provides for a new use of the sporopollenin material (natural or man-made) in chemically-resistant coatings and barriers, which can, themselves, be selectively etched or degraded as necessary.

A preferred embodiment is directed towards a chemical composition comprising hydrogen peroxide together with a catalase and peroxidase enzymes, suitable for combination together to oxidize sporopollenin.

In a preferred embodiment, a method of degrading sporopollenin comprises combining a first component of hydrogen peroxide, a second component being a catalase and a third component being a peroxidase, wherein the components are combined and applied to sporopollenin; wherein the application of the combined components is suitable for oxidizing and rupturing the wall of the sporopollenin.

A preferred embodiment is directed towards a coating composition comprising a carrier and a sufficient quantity of sporopollenin. The coating composition is an oil, water based, epoxy, polyurethane, acrylic, aklylic, polyester resins, or mixtures thereof. Sufficient quantities of sporopollenin are between 0.01% and 99% of the total weight of the composition. In a particularly preferred embodiment, the sporopollenin comprises between 1.0% and 50% of the total weight of the composition.

In a preferred embodiment, the surface is roughed and then coated with a composition comprising sporopollenin and a carrier; the composition is then cured. In certain embodiments, the curing process requires between 1 hour and 48 hours. In certain embodiments, a curing process requires heat, while in others curing involves application of a solvent or catalyst affecting the carrier. In certain preferred embodiments, the carrier and sporopollenin are brushed or sprayed onto the surface, while in others, the carrier and sporopollenin are rolled and pressed onto the surface, creating a non-toxic chemically resistant barrier having antioxidant properties.

In a further embodiment, the sporopollenin-degrading composition comprises a horseradish peroxidase, a beef liver catalase and hydrogen peroxide, which are combined and applied to sporopollenin pollen walls, wherein the composition oxidizes and degrades the materials. In further embodiments, these components are separately housed, before being combined and applied as a combination to the sporopollenin for degrading whole grains or crushed walls of sporopollenin.

These embodiments are directed to uses of sporopollenin for applications where an inert coating material is needed. For example, sporopollenin is suitable for coating a vessel for transport or storage of corrosive, hazardous chemical, or nuclear material, wherein the inert nature of sporopollenin provides for a barrier against corrosion from either the interior or exterior of the vessel.

A preferred embodiment is directed to a composition suitable for degrading sporopollenin comprising: a peroxidase, a catalase, and a peroxide. A preferred embodiment, wherein the peroxidase is a horseradish peroxidase. A preferred embodiment, wherein the catalase is a beef liver catalase. A preferred embodiment, wherein the peroxide is hydrogen peroxide. A preferred embodiment, wherein the peroxidase, catalase and peroxide are stored in separate containers, and combined together to form the composition. A preferred embodiment, wherein the composition is applied to sporopollenin.

A further preferred embodiment is directed towards a method for degrading sporopollenin comprising: forming a composition of a peroxidase, a catalase, and a peroxide; and applying the composition from (a) to sporopollenin. In a preferred embodiment, wherein the sporopollenin is selected from those sporopollenin wherein pollen tubes emerge through inter-aperture walls. A preferred method comprises step (c): washing the composition from the sporopollenin after applying the composition in step (b); and wherein the wash solution may be optionally saved for analysis of its composition, or harvest of its contents.

A preferred embodiment is directed towards a composition comprising a sporopollenin-based matrix suitable for use as an inert coating for a surface, wherein the sporopollenin is admixed with a carrier suitable to create an inert and long-lasting barrier when applied to said surface, wherein such a composition may be suitably removed or etched away from the surface by application of a second composition comprising a peroxidase, a catalase, and a peroxide. A preferred embodiment comprises wherein the peroxidase or catalase is non-naturally occurring. A preferred embodiment comprises wherein the peroxidase and catalase are generated from different species. A preferred embodiment comprises wherein the matrix is at least 2 pollen grains thick. A preferred embodiment comprises wherein the carrier is selected from the group consisting of and oil, water based, epoxy, polyurethane, acrylic, aklylic, polyester resins, or mixtures thereof. A preferred embodiment comprises wherein the ratio of carrier to sporopollenin is between 10:1 and 1:10. A preferred embodiment comprises wherein the composition comprises a carrier is a solid, non-solid, or liquid at room temperature. A preferred embodiment comprises wherein a liquid carrier can be applied to a surface in liquid form. A preferred embodiment comprises wherein a non-solid carrier can be applied to a surface by rolling the non-solid carrier onto the surface. A preferred embodiment comprises wherein the carrier is cured by application of a solvent or catalyst.

A further preferred embodiment comprises a method of coating a surface with a carrier and sporopollenin, comprising washing the sporopollenin, milling the sporopollenin to an average size of 25 micron; adding the milled sporopollenin to said carrier at a ratio of between 100:1 and 1:100; applying the carrier with sporopollenin to the surface and curing the carrier to form a barrier. In certain applications, it is appropriate to rough the surface to allow for better adhesion of the carrier to the surface. In preferred embodiments, the carrier and sporopollenin are a liquid, which can be applied to the surface with an aerosol, a spray or misting agent, a spray gun, a brush or other liquid applicator. In preferred embodiments, the composition of carrier and sporopollenin is a putty or non-solid, which is of sufficient viscosity that it cannot be applied by the liquid methodologies, but is applied with an applicator and rolled or compressed onto the surface. In each case, the carrier is dried or cured based upon the necessary parameters to form the barrier.

Together, the embodiments herein describe a sporopollenin coating material, composed of a carrier and a concentration of sporopollenin suitable to generate a barrier, which can then intentionally be ruptured through the application of hydrogen peroxide, a catalase, and a peroxidase. The product, however, would not be ruptured by ionizing radiation, $H_2SO_4$, HCl, $HNO_3$, HBr, HI, $HClO_4$, or $HClO_3$.

BRIEF DESCRIPTION OF THE DRAWINGS

FIGS. 6A-6C depict rolled steel coated in three protectants, each with sporopollenin (A,B,C) or without (a,b,c) sporopollenin additives. FIG. 6A (A) with sporopollenin, a) without sporopollenin Kilz, Total One Premium stain blocking primer, interior/exterior, water base; FIG. 6B (B) with sporopollenin, b) without sporopollenin Valvoline Full Synthetic Grease; FIG. 6C (C) with sporopollenin, c) without sporopollenin, Turtle wax, Super hard shell paste wax. Coated plates were suspended in a box and fogged continuously for 96 hours with 5% NaCl in water, in accordance with ASTM B-117.

DETAILED DESCRIPTION OF THE EMBODIMENTS

Sporopollenin is a chemically resistant, inert material, being unaffected by any but a few select chemicals, which we find, when combined together, can degrade sporopollenin. This occurs in a natural state, with a material that is widely available, being naturally produced in the amount of tons per year, all over the world. Interestingly, sporopollenin has also found reception in the health care industry, as the material has been shown to have certain antioxidant properties. Accordingly, sporopollenin is consumed orally by some to obtain the benefit of these properties, or applied topically for cosmetic purposes.

The ability of sporopollenin to remain inert despite attacks from acids, bases, UV, heat, cold, etc., underlies its possible use as an inert barrier. However, the fact that the material, to date, has been impenetrable, has limited its commercial application. Herein, we describe methods and compositions for selective degradation of sporopollenin, which gives rise to increased commercial use in other aspects described herein. Furthermore, that sporopollenin is non-toxic provides for a distinct advantage over currently available, commercially-formulated compositions.

Lead and chromium based paints have been commercialized for more than 100 years, in an effort to protect against and reduce oxidation. Despite the growing demand for less toxic alternatives, elimination of hexavalent Chromium (Cr6+) and other metals from the metal finishing industry remains a multibillion-dollar challenge. The 2000 film Erin Brockovitch depicts one example of a legal case resulting from Pacific Gas and Electric's use of hexavalent Chromium to control corrosion in its cooling towers. Contamination of the groundwater in nearby Hinkley, Calif. led to a settlement for $333 million dollars.

Contamination in Hinkley, Calif. is a warning for those in the industry, who have long been aware that our paints and coatings till now have polluted both ground and water throughout the world. One of the biggest concerns and uses of coatings is to protect steel and other metals from oxidation (rust). The Golden Gate Bridge is famously in continuous repair in an effort to prevent oxidation and weakening of the structure. Similarly, other bridges, train tressels, underpasses and the like are constantly bombarded by natural elements leading to degradation, unless they are coated with one or more of these potentially toxic coatings. Similarly, modern military boats, planes, trains, and other vehicles require on-going surface maintenance to limit their costly oxidation and damage. Toxic coatings, however, endanger our troops and environment.

Sporopollenin, offers unique benefits, as it is a low cost, inert substance, available in large quantities. Sporopollenin offers an alternative to metal alloys, metal containing paints and electrolytic protection against corrosion, by serving as both a barrier and an anti-oxidant, thus providing in one substance properties traditionally requiring multiple additives. Thus, we describe herein, compositions to degrade sporopollenin, compositions composed of a carrier and sporopollenin, and methods for oxidizing or etching the surface of sporopollenin.

Sporopollenin Rupture

Sometimes when pollen is dusted onto a stigma, it touches at a grain's aperture, but often a grain lies so that the shortest path from its interior to the stigma is across inter-aperture pollen wall. When this happens in *A. thaliana*, tube cells can take that shortest path; they aim directly through the interface (Edlund et al., 2004), toward the source of stigma fluid (Edlund et al., 2016). As a desiccated grain hydrates, the pectin-rich intine underlying the contact point with the stigma swells (Hoedemaekers et al., 2015). We previously used atomic force microscopy to find that the inter-aperture wall is an order of magnitude stiffer than the material covering the aperture (Edlund et al., 2016), but we measured these properties in pollen growth medium, not on the stigma, and it remained to be seen: 1) if the wall at the break-out site might be weakened in situ by more than simple mechanical strain, and 2) if it were weakened, then by what biochemistry.

We now report that during such germination, the pollen wall is both chemically weakened and mechanically broken. At pollination, factors carried on the pollen surface are able to mix with factors on the stigma surface in a reaction that locally oxidizes the exine pollen wall. Hydrogen peroxide, catalases and peroxidases are present at the right time and place and, when mixed, are experimentally sufficient to degrade the walls of susceptible pollen. Our report of biochemistry employed naturally to breech the inter-aperture wall could aid in the long-sought characterization of sporopollenin (and thus, it's eventual commercial synthesis) and raise questions about aperture evolution and use across taxa.

Natural Degradation of Sporopollenin

Figure 1A:
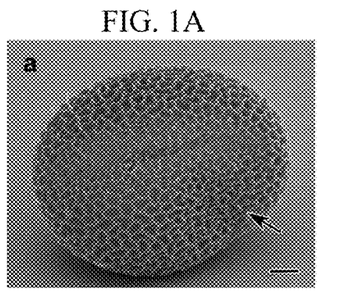
FIGS. 1A-G depict that the sporopollenin exine degrades and thins, while cellulosic and pectin-rich intine swells, when *A. thaliana* pollen germinates between apertures.
Figure 1B:
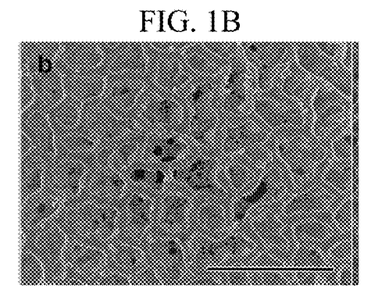
Figure 1C:
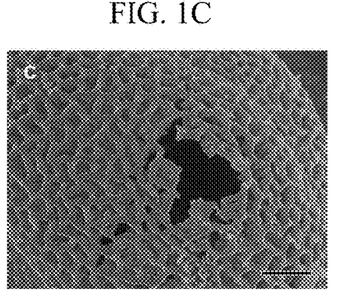
Figure 1D:
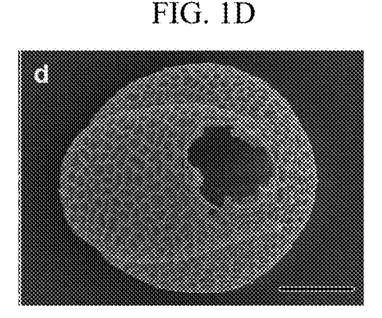

We hand-pollinated and fixed *A. thaliana* stigmas in a time series, using concentrated sulfuric acid and acetolysis to remove everything except the sporopollenin ghosts of the germinating pollen grains, which we viewed with scanning electron microscopy (SEM). Eight minutes post-pollination, we saw that these ghosts are flattened at their interface with the stigma (FIG. 1a). Several minutes later, the nexine layer becomes fenestrated at the floors of the lacunae (FIG. 1b). 12-15 minutes after pollination, larger rips are visible in the nexine, and the baculae tip sideways, as they lose their rooting in the degraded nexine (FIG. 1c). By 15-20 minutes post-pollination, a single, large hole has formed where the tube is crossing (FIG. 1d).

Figure 1E:
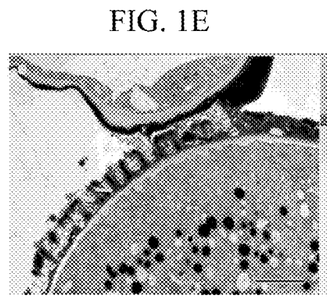
Figure 1F:
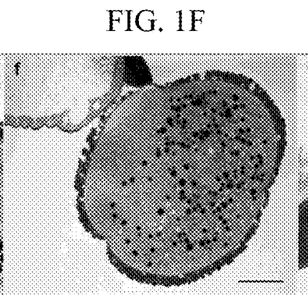
Figure 1G:
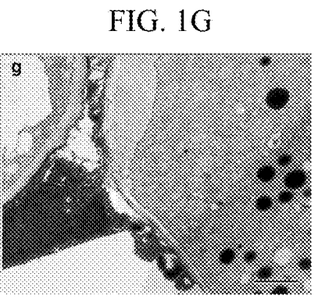

We next used transmission electron microscopy (TEM) to follow *A. thaliana* pollen tube emergence in transect. At eight minutes post-pollination, the vegetative cell is already polarized toward the stigma surface, with visible changes to the plasma membrane and cytoplasm adjacent to the stigma, but without detectable changes to the intine or exine anywhere around the grain (FIG. 1e). Minutes later, the intine has swollen into a lentil shape, the overlying nexine is absent, and overlying sexine architecture is disrupted (FIGS. 1f, g).

FIG. 1 depicts an in situ time series, whereby exine weakens and intine swells during inter-aperture, *A. thaliana* pollen germination; this is shown by scanning (a-d) and transmission (e-f) electron microscopy. SEM, stigmas were fixed at 8-12 (a), 12-15 (b, c), and 15-20 (d) minutes after hand-pollination, then acetolysed (in 90% acetic anhydride, 10% sulfuric acid), critical point dried, and sputter coated. For TEM, stigmas were fixed at 8-12 (e) or 12-15 (f, g) minutes after hand-pollination, post-fixed in 1% $OsO_4$, then 1% uranyl acetate, dehydrated and embedded. Ultrathin sections were stained with 1% uranyl acetate and Reynold's lead citrate. Bars=2 µm in a-e, 4 µm in f, and 1 µm in g.

*A. thaliana*'s pollen germination mechanism can thus be dissected into two parts—a swelling intine pushing against a weakened exine. We next looked for factors at the pollen-stigma contact sites, which could be responsible for local sporopollenin weakening. We envisioned components from the stigma pellicle (call these yellow) and pollen coat (call these red) mixing at their interface or foot (Elleman et al., 1992), and hypothesized that such a mixture (orange) might be responsible for degrading adjacent sporopollenin.

Sporopollenin's Sensitivity to Reactive Oxygen Species

Figure 2A:
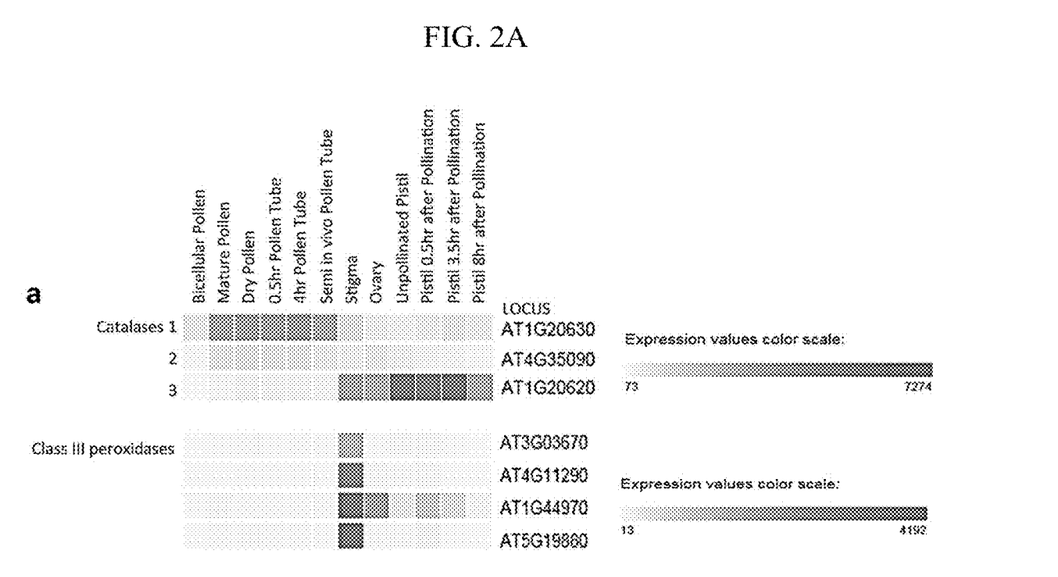
FIGS. 2A and 2B depict that catalases, peroxidases and ROS are present at pollination in *A. thaliana* and other Brassicaceae flowers.
Figure 2B:
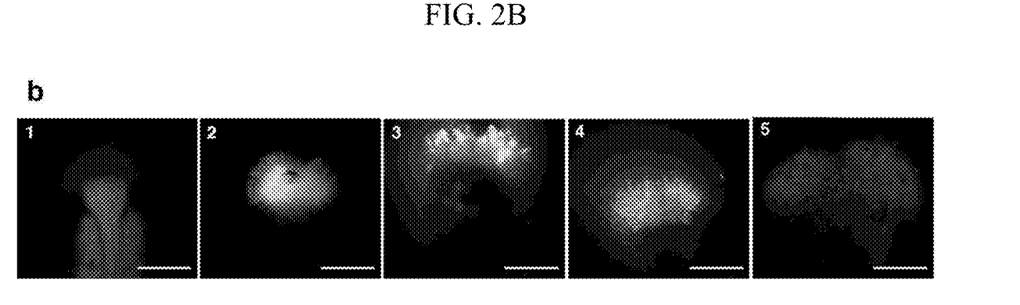
Figure 3:
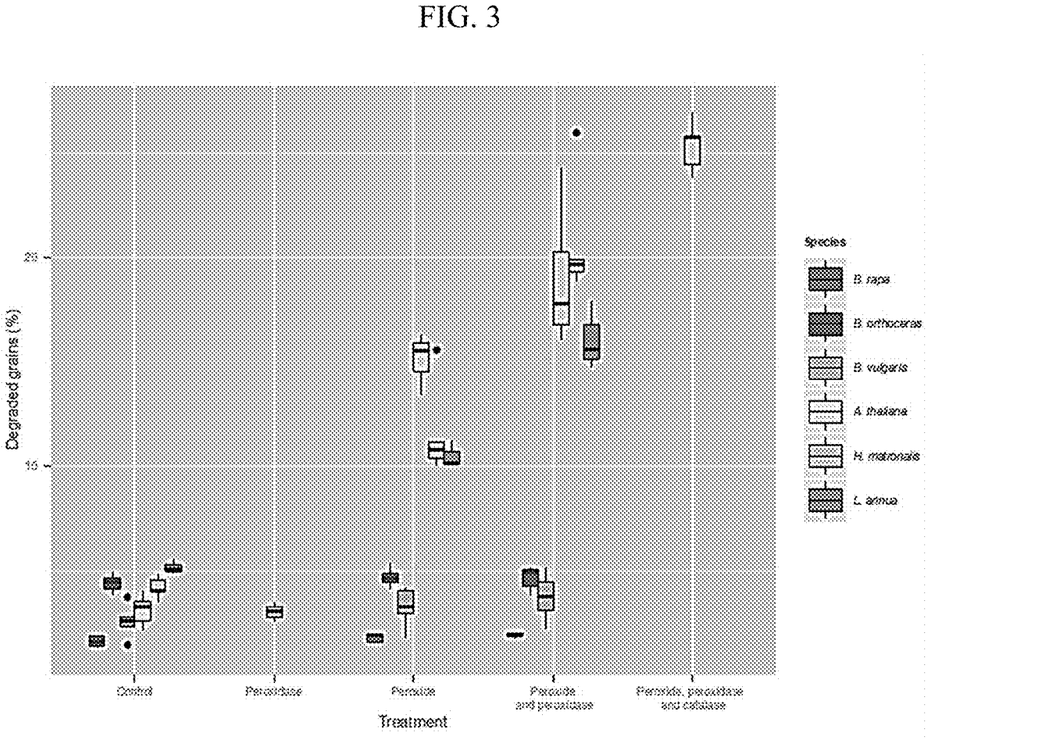
FIG. 3 depicts the percentage degraded Brassicaceae pollen grains following treatment in $H_2O_2$, peroxidase, and catalase.
Figure 4A:
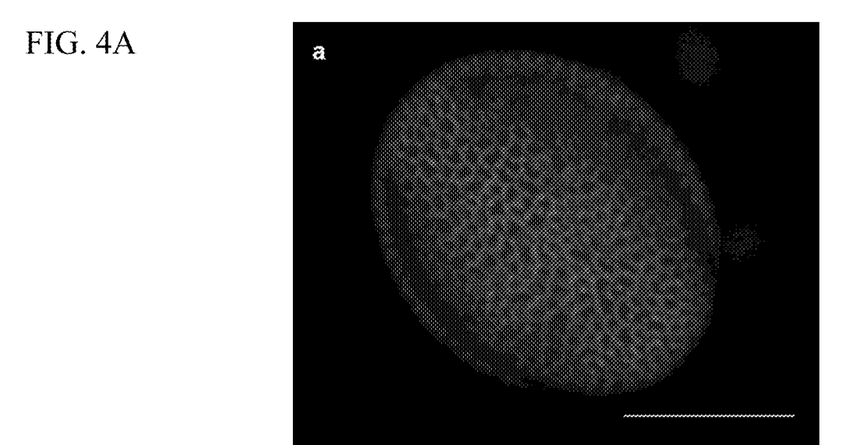
FIGS. 4A and 4B depict a ROS degradation of *A. thaliana* sporopollenin.
Figure 4B:
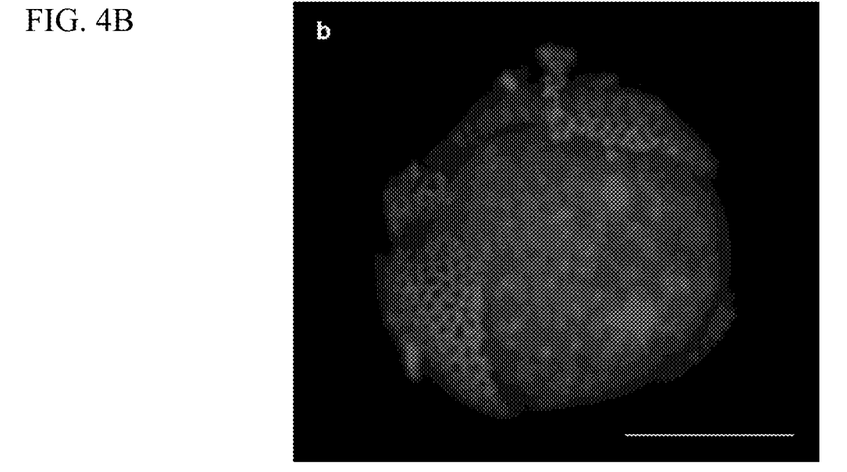
Figure 5:
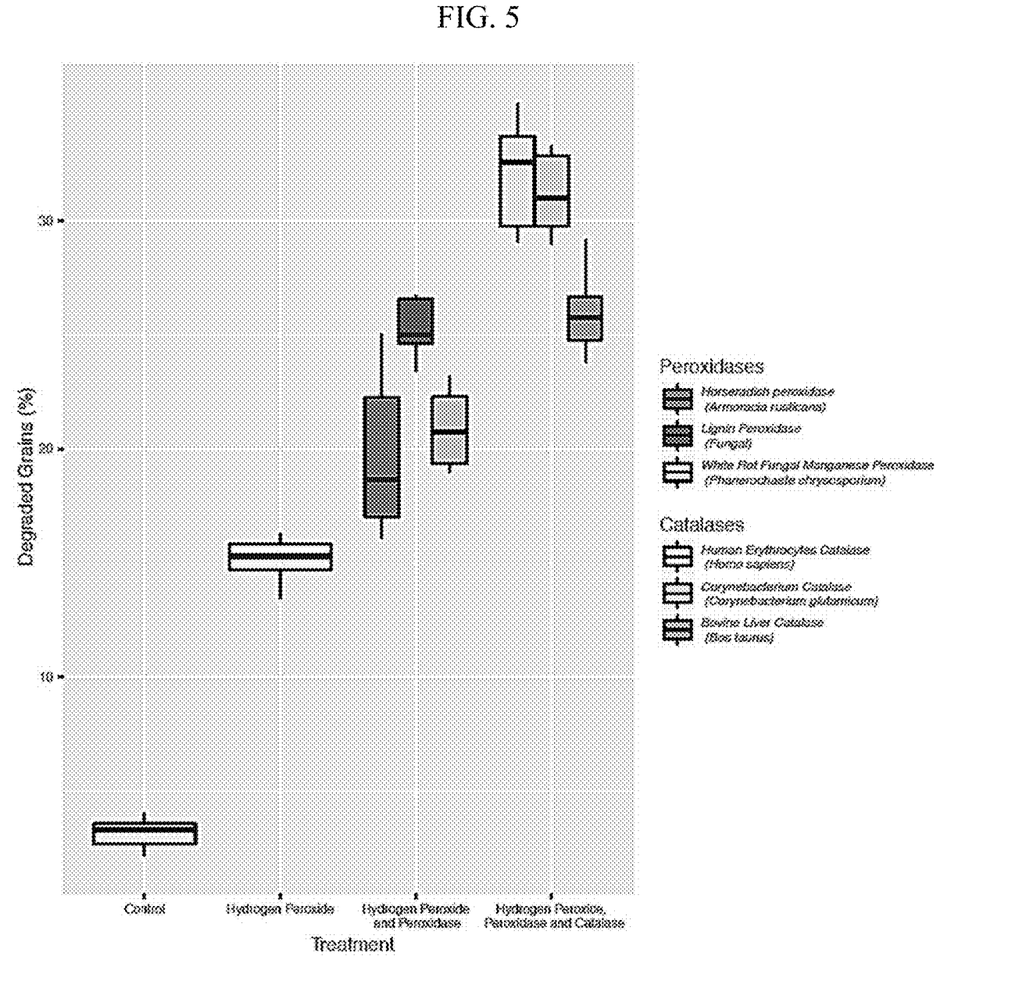
FIG. 5 depicts data for *A. thaliana* sporopollenin degradation by three different catalases and three different peroxidases.

Pollen and stigmas are, in fact, often richly pigmented with red and yellow carotenoids, as in saffron. Such antioxidants protect against oxidative damage from the hydrogen peroxide that covers mature, receptive stigmas in many species (FIG. 2; McInnis et al., 2006a), and from radiation exposure (He et al., 2007). Along with antioxidants and hydrogen peroxide, a number of peroxidases are found at very high levels in stigmas (FIG. 2; Swanson et al., 2005; McInnis et al., 2006b); peroxidase increases have classically been used as assays for stigma receptivity (Galen and Plowright, 1987). Pollen in multiple species, including *A. thaliana*, are known to express high levels of catalase (FIG. 2; Mhamdi et al., 2010), and for nearly a century, pollen catalases have been studied in honey (in the context that both honey and nectar contain hydrogen peroxide; Weston, 2000; Carter and Thornburg, 2004). The three reagents—hydrogen peroxide, peroxidase and catalase—are a famous triplet united in the abdomen of the bombardier beetle, where their exothermic, reduction-oxidation (redox) reaction is well described (Aneshansley et al., 1969). We suspected that a similar reaction, at the site of pollination, could oxidize the sporopollenin wall locally, helping to release the escaping pollen tube. In the absence of these specific parameters, sporopollenin remains inert. We have taken advantage of this natural instance of sporopollenin wall degradation in *A. thaliana* to reveal the biochemistry employed by the flower and have then mimicked it experimentally and on a larger scale.

Synthetic Sporopollenin Degradation

To experimentally mimic the redox reactions of pollination, we bathed *A. thaliana* pollen in commercially available hydrogen peroxide mixed with peroxidase (from horseradish) and catalase (from beef liver). After fluorescently staining the treated sporopollenin with Auramine O, we found that one quarter of the pollen was fragmented and/or globally degraded.

Therefore, a composition suitable for degradation of sporopollenin comprises a first component of a peroxidase, a second component of a catalase, and a third component of hydrogen peroxide. Importantly, the materials are combined using off-the shelf reagents that are suitable for industrial and commercial use. The components, however, cannot be combined into a single entity, they must be combined at the point of use. Accordingly, it would be appropriate to use a multichambered applicator (as often used with things like 2-part epoxy) to provide the appropriate corresponding components together. Once combined, the oxidation reaction proceeds and can degrade the sporopollenin wall.

In a preferred embodiment, a system for degrading sporopollenin walls comprises three components (a peroxidase, catalase, and hydrogen peroxide), suitably admixed together and applied to sporopollenin walls to degrade the material.

Indeed, in order to determine the specific needs of the peroxidase and catalase, we examined several of each of these compounds, not naturally found in or around the sporopollenin pollen grains, to ascertain the class of compounds that may be suitable for commercial degradation of sporopollenin material. The results of these tests are provided in FIG. 5, comprising testing of bovine liver catalase, *Corynebacterium* catalase, and human erythrocytes catalase. These were tested with horseradish peroxidase, lignin peroxidase and white rot fungal manganese peroxidase.

Accordingly, as depicted in FIG. 5 certain peroxidases were tested in combination with hydrogen peroxide. The goal was to evaluate whether any peroxidase would have the same functional effect as another peroxidase, thus identifying the class of effective compounds. Horseradish peroxidase, lignin peroxidase, and white rot fungal manganese peroxidase were each more effective than the control or hydrogen peroxide treatment alone. Furthermore, when these components are further combined with various catalases from different species (Human, *Corynebacterium*, and bovine liver), FIG. 5 shows an additive effect. Sporopollenin degradation increases over that seen by hydrogen peroxide and peroxidase together; in other words, the tripartite mixture is more effective than the bipartite.

FIG. 5 details percentages of degraded pollen grains following different hydrogen peroxide/peroxidase/catalase treatments of *A. thaliana* pollen. In these Tukey box plots, the median is represented by the bold line in the center of each box. The bottom and top of the box represents the $1^{st}$ and $3^{rd}$ quartile of the data, respectively. The whiskers below and above each box represent the lowest and highest value within 1.5 times the interquartile range, respectively. A Wilcoxon Rank-Sum test was used to compare every peroxidase type with hydrogen peroxide alone and the different catalase types with the horseradish peroxidases. All values proved to be significant ($p<0.01$).

Knowing the classes of compounds suitable for degradation of the sporopollenin cell wall is important for commercial principles, wherein formulation of these materials could be easily and inexpensively manipulated into a commercial kit sufficient to degrade and expose a surface previously covered by a sporopollenin-based barrier.

For example a kit may include a concentration of three components, a hydrogen peroxide, a catalase, and a peroxidase. These components need to be kept separate and only combined when they will be applied to a surface, much in the same way that a two-part epoxy is separated before use. Accordingly, a three barrel syringe may be utilized that individually holds the components, and provides them in a volume that allows for the appropriate concentration of each component to be expressed with a single press of a plunger. The materials can be added to a secondary holding device, or applied directly to a surface. Application to a surface made of sporopollenin and a binder would necessitate a sufficient amount to break through the surface.

FIG. 2 depicts that catalases, peroxidases and ROS are present at pollination in *A. thaliana* and other Brassicaceae flowers. a) Heat maps display microarray RNA abundance data for three catalase and four peroxidase genes (scale given at the right, http://arabidopsis-heat-tree.org). Gene expression values are shown for stages of pollen development (bicellular, mature, and dry pollen [Honys and Twell, 2004]), pollen tubes grown in vitro (0.5 hour pollen, 4 hour pollen [Qin et al 2009]), pollen tubes that grew through pistil tissue (Semi in vitro [Qin et al 2009]), the stigma and ovary [Swanson et al 2005], the unpollinated pistil, and pollinated pistils (0.5, 3.5, and 8 hours after pollination [Boavida et al 2011]). b) Carpels stained for ROS. 1) *A. thaliana* carpel treated with 100 mM Na-pyruvate (a hydrogen peroxide scavenger) then stained with 50 mM 2,7-Dichlorodihydrofluorescein diacetate ($DCFH_2$); 2) *A. thaliana,* 3) *Arabis pycnocarpa,* 4) *Armoracia rusticana,* 5) *Brassica rapa* carpels, respectively, stained with $DCFH_2$ to reveal the presence of ROS on each stigma. Bars=0.5 mm Not only could the three-part mixture of hydrogen peroxide, peroxidase and catalase degrade *A. thaliana* sporopollenin, but the two-part mixture of peroxidase and hydrogen peroxide degraded a smaller percentage, and hydrogen peroxide, alone, an even smaller percentage; peroxidase enzyme by itself did not degrade pollen walls (FIG. 3). Confocal laser scanning microscopy reveals the changed surface of *A. thaliana* pollen grains following treatment with hydrogen peroxide (FIG. 4), despite this sporopollenin's evident complete resistance to acetolysis (FIG. 1).

FIG. 3. Addresses the percentage degraded Brassicaceae pollen grains following treatment in $H_2O_2$, peroxidase, and catalase. The three species that germinate only through apertures (Reds; *Brassica rapa, Barbarea orthoceras, Barbarea vulgaris*) showed low sensitivity to ROS degradation and no significant variation between treatments, with species considered as an error term (F value=3.78, p=0.12 by ANOVA), whereas the three species that germinate by break-out (Blues; *Arabidopsis thaliana, Hesperis matronalis, Lunaria annua*) differed between the treatments, with species considered as an error term (F value=47.1, p=0.0016 by ANOVA). For *A. thaliana*, all pairwise differences were significant (below p=0.01) except the pair control and peroxidase (p=0.99 Tukey I-ISD). Treatments differed significantly between break-out and non-break-out species, but only slightly for the control (p values<0.001, <0.001 and 0.160, Wilcoxon rank sum test with Bonferroni correction). Boxes represent interquartile range, with line as median and whiskers as highest and lowest points within 1.5 times the IQR.

FIG. 4 depicts ROS degradation of *A. thaliana* sporopollenin. Confocal laser scanning micrographs of pollen grains after they were fixed in ½ strength Karnovsky's, treated for one hour in either a) $KH_2PO_4$ buffer or b) 12.5% hydrogen peroxide, washed, and then fluorescently stained with 0.1% Auramine O. Bars=10 μm.

To determine if pollen grains of other species would be similarly sensitive to these reactive oxygen species (ROS), we treated pollen grains from three obligate aperture users (*Brassica rapa, Barbarea vulgaris* and *Barbarea orthoceras*), and three break-out species able to germinate through inter-aperture walls (*A. thaliana, Lunaria annua,* and *Hesperis matronalis*; Edlund et al., 2016). By fluorescence microscopy, we found that only species with natural inter-aperture germination were detectably sensitive to experimental redox wall degradation (FIG. 3). Therefore, the effect here is limited to pollen from species in which pollen tubes emerge through inter-aperture walls, or by what is called "omni-aperturate" germination (Edlund et al., 2016).

With so much variety in pollen grain and stigma structures, a single aperture-based model of pollen germination won't apply to all taxa. An alternative, functionally omni-aperturate model is found in *A. thaliana*, and ~25% of other surveyed Brassicaceae, by which cells escape the pollen grains through holes in the walls between apertures. We report here the involvement of redox reactions in degrading these holes, and a simple reagent mixture that can be exploited further for material science application.

In the natural plant model, at pollination, pollen grains contact hydrogen peroxide-covered stigmas. For sensitive species, we found that hydrogen peroxide alone is sufficient to alter the pollen wall, with degradation increasing if peroxidase and catalase enzymes are added. We believe that when catalase mixes with stigma hydrogen peroxide, the hydrogen peroxide decomposes, producing heat and short-lived reactive oxygen radicals, which act with stigma peroxidases to oxidize nearby sporopollenin. Other ROS-associated factors that localize to stigma and pollen at the time of pollination, and may further affect biochemistry at the interface, include: superoxide dismutase (Speranza et al., 2012), nitric oxide (McGinnis et al., 2006a), glutathione (Zechmann et al., 2011), NADPH respiratory burst oxidase homologs (RBohs; Jimenez-Quesada et al., 2016), and dietary antioxidants (Alicic et al., 2014). Reminiscent of the bombardier beetle's redox reactions, a pollen hydroquinone alternative called Tasselin has also been identified (Wille and Berhow, 2011). In preliminary studies with a bomb calorimeter, we are detecting small increases in temperature (0.0005 degrees) when multiple stigmas are simultaneously dusted with pollen (data not shown), consistent with catalase's exothermic decomposition of hydrogen peroxide. Note that thermogenic flowers, such as the lotus, use a distinct mechanism to make heat for pollinator reward, although their rise in flower temperature is synchronized with a rise in stigma peroxidase expression (Seymour and Blaylock, 2000).

Sporopollenin is a dynamic, changeable substance inside flowers, even if it is unchangeable elsewhere. As it forms in the anther, and first becomes resistant to acetolysis, it may be cross-linked by peroxide radicals (Scott, 1994). If it is later weakened by oxidation on the stigma, sporopollenin may regain its sensitivity to acetolysis (although we have yet to try treating *A. thaliana* pollen sequentially with ROS and then acetolysis solutions). Our report of localized exine degradation in the Brassicaceae joins several past reports, for other species, of more global changes to exine at the time of pollination, such as spines melting and walls becoming amorphous or altered in their staining (Gherardini and Healey, 1969; Dickinson and Lewis, 1974; Rowley and Rowley, 1983). Wall disintegration is also described during spore germination in the protist *Chlamydomonas monoica* (Malmberg and VanWinkle-Swift, 2001). One future line of research would be to explore fertile, inaperturate pollen (found in over 50 families), looking for additional mechanisms of sporopollenin degradation—given that even cells in inaperturate grains must have a means of escape.

Our research accentuates the need for systematic surveys of pollen germination mechanisms. Other pollen tubes will be found that fail to emerge at apertures, and other sporopollenin that fails to resist degradation, but with what systematic patterns? There is an evolutionary trend in angiosperms for an increase in aperture number; inaperturate and monosulcate pollen are common among basal angiosperms and monocots, whereas eudicots most frequently have three apertures or more. Increasing numbers of apertures, and thus germination sites, would seem to offer a selective advantage (Furness and Rudall, 2004), as would the ability to germinate anywhere, directly through exine walls. It is possible that the true apertures retained in functionally omni-aperturate pollen are used when grains fall aperture-side down, and to allow volume change, fluid and signal movement. The intine swelling/exine weakening steps we describe could be specific to germination in the Brassicaceae (and to species having dry stigmas, thin exine, tri-cellular pollen, and rapid germination), and they seem to have evolved more than once in this family (Edlund et al., 2016).

Formation of Sporopollenin Coatings

Figure 6A:
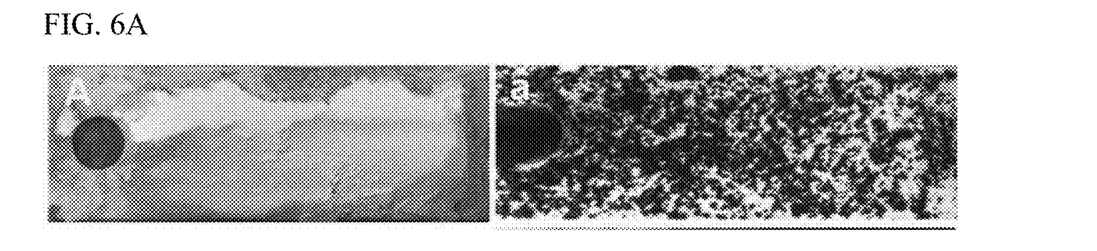
Figure 6B:
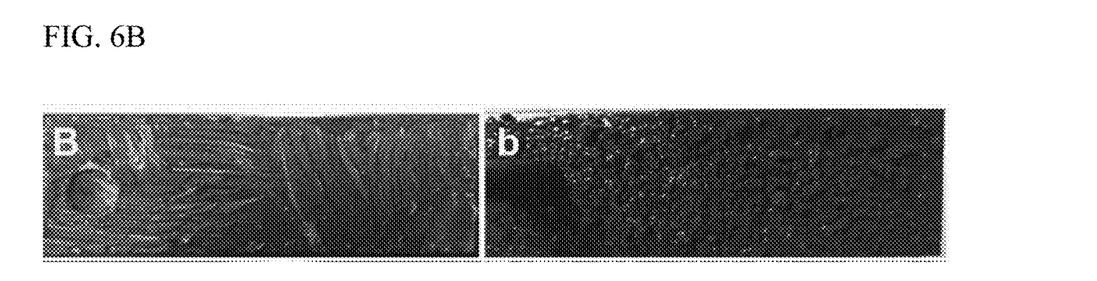
Figure 6C:
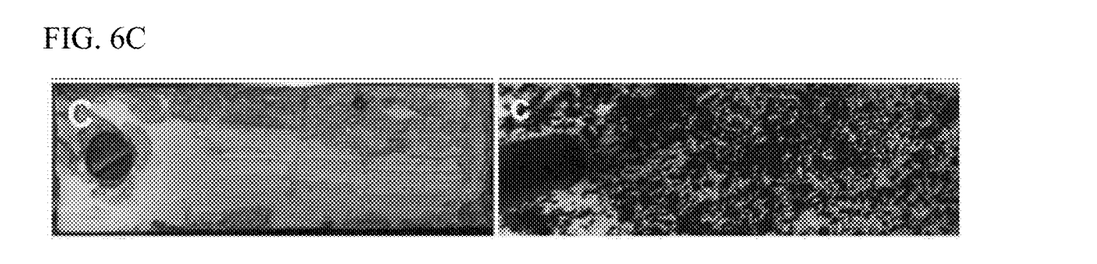

Having the ability to degrade the sporopollenin, we envisioned that sporopollenin could be advantageously used as an inert barrier and antioxidant material. To test these coatings, and as proof of principle for the utility of sporopollenin in chemically resistant coatings, we have added sporopollenin (in this case naturally-sourced, but in eventual case this could be laboratory synthesized) to existing metal protective formulations and have shown decreased oxidation of steel plates following ASTM B-117 treatments. The results of these tests are depicted in FIG. 6, showing coatings alone and with sporopollenin.

Many existing coatings are formulated to contain both a barrier component and an antioxidant component. However, toxicity (especially in the antioxidant component) is a major problem for existing coatings. Accordingly, these coatings often contribute to environmental contamination Tonnes of pollen cell walls are available for harvest annually from fields and woodlands. Uniquely long-lasting and chemically unreactive, sporopollenin could be developed for lining nuclear or chemical waste containers, or for industrial or biomedical coatings. The material behaves as a strong and species-specific adhesive on the stigma surface (Zinkl et al., 1999) and even self assembles, forming ornaments and contours by physical, rather than purely genetic, means (Blackmore et al., 2007). To date, however, sporopollenin's intractability has slowed progress on determining its composition and on developing applications. The redox reactions we describe here provide an early step toward characterizing and exploiting this material that persists thousands of years, withstands hydrofluoric acid, and yet degrades with the simple tripartite combination of hydrogen peroxide, peroxidase, and catalase at the moment of pollination.

Sporopollenin is a promising corrosion-resistant coating component, but its use as a coating material is somewhat limited, if we cannot subsequently reverse, remove or break down the material. As described herein, we can now selectively degrade sporopollenin with a cocktail of hydrogen peroxide, a peroxidase, and a catalase, making sporopollenin-based linings or coatings now removable.

For example, suitable coating materials may comprise a coating of a portion silicone, crosslinked with other suitable materials, and binding therein a portion of sporopollenin. In a preferred embodiment, the sporopollenin is bound in a single layer, wherein the binding of the silicone material, holds the sporopollenin together in a closely held structure. Certain preferred embodiments comprise sporopollenin bound in a multi-layer structure, wherein the sporopollenin coating is two or many more pollen grains thick, thereby creating a three-dimensional wall.

In certain embodiments, a resin based material is suitably utilized. For example, a core/shell resin is used in which an acrylic rubber resin forms the core and the epoxy resin, preferably a bisphenol A epoxy resin, forms the shell. Again, chemical bonding between carboxylic functionality of the acrylic rubber resin of the core and the epoxy resin of the shell prevents phase separation during fusion and curing of the coating powder formed using the core/shell resin. Such acrylic rubber modified epoxies are described, for example, in Polymer Reprints, 32(3), pp. 358-9 by H-J Sue and E. I. Garcia-Melfin.

Further options for suitable resins include thermosetting epoxy resins. Such thermosetting epoxy resins may include either a cross-linking agent, such as a polyhydroxyl compound or a cure catalyst to effect auto-cross-linking of the epoxy resin. For example, the epoxy resin is cured with a polyhydroxyl functionality having a relatively high hydroxy equivalent weight, i.e., at least about 200 up to about 500, preferably at least about 300. The relatively high hydroxy equivalent weight of the cross-linking agent ensures relatively long chain length between OH groups, which chain lengths provide flexibility to the cured coating, helping to render the coatings chip-resistant. Notably, this feature provides for sufficient flexibility to incorporate pollen grains into the structure. Preferential materials bind to the sporopollenin wall both mechanically and chemically and allow pollen to be arrayed within the resin at sufficient concentration and contact with other pollen grains to prevent degradation of the coating, except by hydrogen peroxide, peroxidase, and catalase material, as described herein.

In an effort to cure the material, suitable curing agents useful in the practice of this invention are exemplified by phenolic curing agents, such as a bisphenol A, end-capped diglycidyl ether of bisphenol A, which is the reaction product of a diglycidyl ether of bisphenol A, and bisphenol A and polyester resins with free carboxylic acid groups that are known to form "Hybrid" powder coatings. Examples of preferred phenolic curing agents for the epoxy resin component include those sold under the trademarks D.E.H.™87 and D.E.H.™85 (Dow Chemical Co.), both of which are believed to be bisphenol A end capped diglycidyl ethers of bisphenol A. Other classes of phenolic hardeners can be used as well such as phenol- and cresol-novolac curing agents sold by Dow Chemical Co. Hexion Specialty Chemicals.

Other epoxy crosslinking agents include, for example: amines, including multifunctional aliphatic or aromatic primary or secondary amines, such as dicyandiamide, diaminodiphenyl sulfone; tertiary amines which promote self crosslinking such as DMP 30 (Dow Chemical Co.); boron trihalides and salts thereof such as the monoethanolamine salt of boron trifluoride; organic acid salts such as VESTAGON™B55 and VESTAGON™B68 (Degussa Corp.); di and poly anhydrides such as benzophenonetetracarboxylic dianhydride (BTDA); di and poly phenols such as methylene disalicylic acid; and, imidazoles, substituted imidazoles and epoxy imidazole adducts such as 2-methyl imidazole or DEH 40 (Dow Chemical Co.). Those of skill in the art will recognize these particular epoxy agents and their suitable use as a carrier and a component in combination with sporopollenin.

Compositions of the above resins or silicone-based materials include preferentially between 1-99% by weight sporopollenin grains, but may optionally include other corrosion inhibiting materials, pigments, or materials indicated for increasing the elasticity, or rigidity, as appropriate, of the material. Preferred embodiments comprising compositions of 5%, 10%, 15%, 20%, 25%, 30%, 35%, 40%, 45%, 50%, 55%, 60%, 65%, 70%, 75%, 80%, 85%, 90%, 95%, sporopollenin by weight of the total weight of the composition. These ranges include all particular numbers, and also unspecified numbers in between 1-99%.

Application of the coating material may be by several known mechanical strategies. For example, the material may be combined in a two-part like epoxy medium, and applied to a surface as a liquid or pliable material, such as a putty. The liquid material can be sprayed onto a surface, assuming sufficient density of sporopollenin and viscosity of the carrier liquid. The putty like material can be rolled onto a surface, e.g. as necessary to fix a hole in a material, or to otherwise be rolled flat as a resistant coating onto a surface. Examples of certain suitable material include those as described in US 2010/0266459 and US 2010/0256282, US 2011/0070376, U.S. Pat. No. 5,026,517, or as described in http://sti.srs.gov/fulltext/SRNL-STI-2013-00224.pdf.

Methods

Plant Growth and Field Collection

*Arabidopsis thaliana* plants were from the *Arabidopsis* Biological Resource Center (ABRC) at Ohio State University, Columbus, Ohio, and included: Columbia (Col-4, CS933), Landsberg erecta (Ler, CS20), and Male Sterile-1 (ms-1, CS100). Seeds were sown on soil, stratified at 4° C. for 2 days, and plants were grown under Agrosun fluorescent lights (Hydrofarm, Germany; 100 μE) for 16 hrs/day at ~50% humidity, watered three times weekly, and fertilized once weekly with Miracle-Gro Plant Food (Scotts Company, Marysville, Ohio). *Brassica rapa* (Wisconsin Fast Plant standard, Carolina Biological Supply) was grown from seed in the laboratory, under 24 hrs/day light, but otherwise identical conditions. Flowering *Hesperis matronalis, Barbarea orthoceras* and *Barbarea vulgaris* plants were collected from the roadside near Lafayette College campus in Easton, Pa. May-July, 2015. Flowering *Lunaria annua* was collected from East Lake, Atlanta, Ga. in May, 2015 and replanted in the laboratory. Flowering *Arabis pycnocarpa* and *Armoracia rusticana* were collected from the roadside in Oxford, Pa. in April, 2016.

Electron Microscopy

Preparation of Material by Acetolysis for SEM Observation

Gynoecia were removed from mature ms-1 flowers under a dissecting microscope, and the receptacle was embedded in a thin layer of 1% agar to maintain the water supply. At room temperature and humidity, wild type pollen grains of Landsberg (WT Ler) were manually pollinated onto the stigmas. After waiting periods of 8-12 min, 12-15 min, or 15-20 min, stigmas were placed in 5% KOH w/v, and incubated in an 80° water bath for 10 min, mixing every 2 min. The tube was then centrifuged at 9,250 RCF for 2 min, and the supernatant was discarded. The pellet was resuspended in 300 μl concentrated HCl, mixed well, and water was added to make a total volume of 1 ml. The tube was then centrifuged at 10,000 rpm for 5 min, and the supernatant was discarded. The pellet was resuspended by adding 1 ml glacial acetic acid to the tube, and the tube was then centrifuged at 9,250 RCF for 5 min. After discarding the supernatant, 1 ml acetolysis mixture (90% acetic anhydride, 10% sulfuric acid v/v) was slowly added into the tube. The tube was incubated at 100° C. for about 8 min, with mixing every 2 min, and then centrifuged at 9,250 RCF for 2 min. At this time, a dark brown pellet was visible at the bottom of the tube. The supernatant was removed, and the pellet was resuspended in 1 ml glacial acetic acid. The tube was centrifuged, the liquid discarded, and the pellet either stored in the residual liquid at room temperature, or else directly processed through the next step. The pellet was washed at least three times in distilled deionized water, and left in 50 ul water at the last washing step. The tube was vortexed and about 10 ul of pollen suspension was pipetted out and placed onto a poly-L-lysine coated 5×5 mm silicon chip specimen support (Catalog #16008. Ted Pella Inc.). After waiting for about 1 min so that the pollen debris could precipitate onto the chip, the chip was dehydrated with 10% increments of ethanol, and critical point dried using a Balzers Union CPD20. After mounting the chips onto 15 mm stubs with carbon tape, about 10 nm iridium was coated onto the samples using an Emitech K575X sputter coater. A thin strip of copper tape was used to connect the top of the chip to the base of the stub for grounding. Bleaching methods are also provided in U.S. Pat. No. 8,828,464, and may be suitable for certain sporopollenin applications.

Scanning Electron Microscopy Imaging of Acetolysed Pollen

Samples prepared by acetolysis were imaged on a Hitachi S-4800 scanning electron microscope (SEM) at 5 kV accelerating voltage in secondary (SE) detection mode using the mixed signal from the upper and lower SE detectors.

Specimen Preparation for Ultrathin Sectioning

WT Ler pollen grains were manually pollinated onto the stigmas of receptive ms1 flowers. After 8-12 minutes, 12-15 minutes, 15-20 minutes or 20-30 minutes, pollinated flowers were placed in fixative overnight at room temperature. After rinsing twice in 0.1M HEPES pH7.2, tissues were post-fixed in 1% $OsO_4$ w/v overnight. Samples were rinsed in water twice, followed by overnight fixation in 1% uranyl acetate, dehydration with 10% increments of acetone, and embedding in modified Spurr's resin.

Ultrathin Section Preparation for Transmission Electron Microscopy

Ultrathin (silver to pale gold) sections were cut with a diamond knife on a RMC MT 7000 ultramicrotome and picked up on 200 mesh copper grids. Sections were stained with 1% aqueous uranyl acetate and Reynold's lead citrate, then imaged with a Hitachi H-600 transmission electron microscope operating at 75 kv.

Detection of Reactive Oxygen Species

Carpels were removed from newly opened flowers of each species and soaked in 50☐M. 2,7-Dichlorodihydrofluorescein diacetate ($DCFH_2$; Sigma-Aldrich) in KCl-MES buffer. After 20 minutes staining, carpels were mounted in KCl-MES buffer and immediately viewed on the microscope; all images were captured within 5 minutes of mounting. Some carpels were pretreated for 20 minutes in 100 mM Na-pyruvate (a hydrogen peroxide scavenger) in distilled water, before they were soaked for 20 minutes in 50☐$DCFH_2$ and mounted in KCl-MES buffer.

Experimental Sporopollenin Degradation

Freshly dehisced anthers were collected into ½ strength Karnovsky's fixative (2.5% gluteraldehyde, 2.7% formaldehyde in 15M HEPES buffer, pH 7.4) from each of the six Brassicaceae species. The Columbia accession was used for *A. thaliana* flowers, with 40 flowers worth of anthers (~240 anthers total) fixed in each micro-centrifuge tube. Tubes were vortexed at low speed for 15 seconds to separate pollen from anthers. Anther and filament tissues were removed using forceps. Tubes were centrifuged at 9,250 RCF for 3 minutes, the supernatant removed, and pellets resuspended in subsets of the following: 500 μL, 50% $H_2O_2$, 500 μL $KH_2PO_4$ buffer, 2,360 Units/ml horseradish peroxidase (Thermo Scientific), and 23 Units/ml beef liver catalase (Sigma-Aldrich). Alternatively, similar units/ml of lignin peroxidase or white rot fungal manganese peroxidase or human erythrocyte catalase or *Corynebacterium* catalase (all from Sigma Aldrich) were used. Samples were treated for one hour before spinning at 9,250 RCF for 3 minutes and resuspending in 1 mL of $KH_2PO_4$ buffer, then centrifuging one final time. If samples were to be scored for degradation, they were resuspended in one drop of 0.01% Auromine O stain in HEPES buffer and viewed at 40× magnification with fluorescent microscopy.

Experimental Steel Protection by Addition of Sporopollenin

Honeybee pollen was purchased commercially (Koppert USA) and acetolysed by the concentrated Sulfuric acid and acetic anhydride method described above. This was followed by a defatting step of 2 hours in boiling acetone. For FIG. 6, cleaned sporopollenin shells were ground coarsely (naturally-sourced, cleaned pollen may be prepared in multi-grain clusters, as single ~10 micrometer grains of uniform dimensions, or fractured into fragments smaller than 10 micrometers). Pollen was applied to rolled steel plates along with three simple metal protective agents. The plates were suspended in a salt-water (5% NaCl) fogging box, for 96 hours of continuous fogging, as described for ASTM B-117. Visual examination of the resulting plates revealed over 70% reduction in oxidative discoloration.

In a further example, sporopollenin was prepared by first acetolysed by a sulfuric acid method as described above. The resulting sporopollenin was then post produced into a fine powder through one of several methods. In one example, the sporopollenin was simply pressed through a fine sieve to separate the pollen grains and to create a more uniform grain size. The particular size of sporopollenin simply depends on the species utilized. Typical grains are between 10 to nearly 100 micrometers. For certain purposes, smaller grain sizes are more appropriate, i.e. those of an average size of less than 50 micrometers. Once passed through the fine sieve, the clumps of pollen are reduced. The pollen can be dried in a desiccator and again passed through the sieve before addition to one of the carriers.

A second method of preparing the sporopollenin involves milling. In this case, a portion of sporopollenin is provided into a shaking container, filled with one or more steel or plastic balls. In the case of the plastic balls, the material simply separates the pollen grains to generate a fine size. For use of steel balls, the steel may, in some cases damage and destroy the grains, resulting in an even finer sized grain from the fragments of sporopollenin shells. A further strategy is to use cryomilling, wherein the sporopollenin is frozen or milled under liquid nitrogen temperatures. By reducing the temperature, we make the sporopollenin walls brittle and aid in creation of a fine powder. In each case, the resulting powders are dried through a desiccator or low temperature furnace to allow for uniform mixing into a carrier.

Carriers include waxes (oil based), epoxy, polyurethane, acrylic, alkylic, polyester resins, aqueous based carriers, and mixtures thereof. Preferred embodiments use a ratio of about 100 parts carrier to 1 part sporopollenin. Further preferred embodiments use about 10 parts carrier to 1 parts sporopollenin. Further preferred embodiments use about 5 parts carrier to 1 part sporopollenin. Further ranges include 1 part carrier to 1 part sporopollenin, or to 2, 3, 5, 10, 15, 20, 25, 30 35, 40, 45, 50, 55, 60, 65, 70, 75, 80, 85, 90, 95, and 100 parts sporopollenin. All ranges in between, including those not specifically enumerated are contemplated.

In FIG. 6, we utilized three different coatings alone, and then incorporated pollen into each coating, which served as a carrier. FIGS. 6A and 6a depict Kilz, a water based stain blocking primer. FIG. 6B/b depict Valvoline synthetic grease, and FIG. 6C/c depicts turtle wax, super hard shell paste wax. Each coating (with or without sporopollenin) was applied to a steel plate before being fogged with 5% NaCl in water according to ASTM B-117. For the coating preparations comprising sporopollenin, the sporopollenin was cleaned as above and added to form about a 1:1 ratio of sporopollenin before application.

The results are clear, addition of sporopollenin to each of the carriers dramatically increases the oxidative protection of the underlying steel having about 70% less oxidation than the coatings without sporopollenin. Additional coatings were tested, including coatings intended for use of and prevention of rust. We again added sporopollenin to these coatings and tested under the ASTM B-117 standard. These coatings were of sufficient quality that very faint pitting and oxidation was beginning to occur for the samples alone. However, for the coatings including sporopollenin, we were unable to identify any oxidation for the coatings with sporopollenin. Accordingly, in each case, the addition of sporopollenin assists in preventing oxidation of the surface.

We then tested the ability to remove the coatings from the surface, by first coating a steel rod as in FIG. 6 with a coating comprising Brassicaceae sporopollenin and then, etching spots into the coatings by addition of the compositions for removal. Etching compositions contained hydrogen peroxide, catalase and a peroxidase. The components were combined and then dropped on three spots on each sample. The components were allowed to sit on the sample for 1 hour and then washed with water. After washing, the samples were again misted with salt under ASTM B-117 standard.

As expected, the spots that were etched with the removal components showed dramatic increase in the formation of oxidation, whereas the spots that were not etched remained in their non-oxidized form. Accordingly, we can create a barrier/oxidative protectant to be applied to a surface and now, strategically etch this barrier. This provides that a material could be completely coated with a barrier, strategically etched to allow for, e.g. an electrical contact point, while the rest of the material remains coated with the protective coating. Furthermore, a barrier could be placed over an opening of a closed container and only opened once the coating is removed by application of the hydrogen peroxide, catalase, and peroxidase components.

The ability to utilize sporopollenin as a coating additive provides for a new and unique strategy. The carrier, in combination with the sporopollenin, generates a barrier, preventing contact between, in this case, salt water and the underlying steel surface. The sporopollenin, in certain applications, forms a lattice like structure to enhance the properties of the barrier formation. At the same time, the antioxidant properties of sporopollenin assist in capture of oxidizing agents, and thus prevents or reduces the time for oxidation of the underlying surface. Together, the barrier formation and the antioxidant properties form a unique, non-toxic strategy for barrier formation.

Accordingly, those of skill in the art will recognize that the scope of the embodiments is not limited by the above examples, and that modifications and certain components can be exchanged without departing from the nature of the invention of the compositions, coatings and methods of use of these materials.

REFERENCES

Alicic, D., Subaric, D., Jasic, M., Pasalic, H., and D. Ackar. 2014. Antioxidant properties of pollen. *Hrana u zdravlju i bolesti, znanstveno-strucni casopis za nutricionizam i dijetetiku* 3: 6-12.

Aneshansley, D. J., Eisner, T., Widom, J. M., and B. Widom. 1969. Biochemistry at 100° C.: Explosive secretory discharge of bombardier beetles (Brachinus). *Science* 165: 61-63.

Blackmore, S., Wortley, A. H., Skvarla, J. J., and J. R. Rowley. 2007. Pollen wall development in flowering plants. *New Phytologist* 174: 483-498.

Carter, C. and R. W. Thornburg. 2004. Is the nectar redox cycle a floral defense against microbial attack? *Trends in Plant Science* 9: 320-324.

Dickinson, H. G., and D. Lewis. 1974. Changes in the pollen grain wall of *Linum grandiflorum* following compatible and incompatible intraspecific pollinations. *Annals of Botany* 38: 23-29.

Dominguez, E., Mercado, J. A., Quesada, M. A. and A. Heredia. 1999. Pollen sporopollenin: degradation and structural elucidation. *Sexual Plant Reproduction* 12: 171-178.

Edlund, A. F., Swanson, R., and D. Preuss. 2004. Pollen and Stigma Structure and Function: The Role of Diversity in Pollination. *The Plant Cell* 16: S84-S92.

Edlund, A. F., Zheng, Q., Lowe, N., Kuseryk, S., Ainsworth, K. L., Lyles, R. H., Sibener, S. J. and D. Preuss. 2016. Pollen from *Arabidopsis thaliana* and other Brassicaceae are functionally omniaperturate. *American Journal of Botany* (submitted)

Elleman, C. J, Franklin-Tong, V., and H. G. Dickinson. 1992. Pollination in species with dry stigmas: the nature of the early stigmatic response and the pathway taken by pollen tubes. *New Phytologist.* 121 (3): 413-424.

Erdtman, G. 1960. The acetolysis method. *Svensk Bot. Tidskrift* 54: 561-564.

Furness, C. A. 2007. Why does some pollen lack apertures? A review of inaperturate pollen in eudicots. *Botanical Journal of the Linnean Society* 155: 29-48.

Furness, C. A. and P. J. Rudall. 2004. Pollen aperture evolution: a crucial factor for eudicot success? *Trends in Plant Science* 9: 154-158.

Galen, C. and R. C. Plowright. 1987. Testing the accuracy of using peroxidase activity to indicate stigma receptivity. *Canadian Journal Botany* 65: 107-111.

Gherardini, G. L., and P. L. Healey. 1969. Dissolution of outer wall of pollen grain during pollination. *Nature* 224: 718-719.

He, J.-M., Bai, X.-L., Wang, R.-B., Cao, B., and X.-P. She 2007. The involvement of nitric oxide in ultraviolet-B-inhibited pollen germination and tube growth of *Paulownia tomentosa* in vitro. *Physiologia Plantarum* 131: 273-282.

Heslop-Harrison, Y., and J. Heslop-Harrison. 1992. Germination of monocolpate angiosperm pollen: evolution of the actin cytoskeleton and wall during hydration, activation and tube emergence. *Annals of Botany* 69: 385-394.

Hoedemaekers, K., Derksen, J. Hoogstrate, S W., Wolters-Arts, M., Oh, S.-A., Twell, D., Mariani, C., and I. Rieu. 2015. BURSTING POLLEN is required to organize the pollen germination plaque and pollen tube tip in *Arabidopsis thaliana*. *New Phytologist* 206: 255-267.

Jimenez-Quesada, M. J., Traverso, J. A. and J. de Dios Alche. 2016. NADPH Oxidase-dependent superoxide production in plant reproductive tissues *Frontiers in Plant Science* 7:359.

Malmberg, A. E., and K. P. VanWinkle-Swift. 2001. Zygospore germination in *Chlamydomonas monoica* (Chlorophyta): timing and pattern of secondary zygospore wall degradation in relation to cytoplasmic events. *Journal of Phycology* 37: 86-94

McInnis S. M., Desikan R, Hancock J. T., and S. J. Hiscock. 2006a. Production of reactive oxygen species and reactive nitrogen species by angiosperm stigmas and pollen: Potential signaling crosstalk. *New Phytologist* 172: 221-228.

McInnis, S. M., Emery, D. C., Porter, R., Desikan, R., Hancock, J. T. and S. J. Hiscock. 2006b. The role of stigma peroxidases in flowering plants: insights from further characterization of a stigma-specific peroxidase (SSP) from *Senecio squalidus* (Asteraceae). *Journal of Experimental Botany*. Oxygen Metabolism, ROS and Redox Signaling in Plants Special Issue 57: 1835-1846.

Mhamdi, A., Queval, G., Chaouch, S., Vanderauwera, S., van Breusegem, F. and G. Noctor. Catalase function in plants: a focus on *Arabidopsis* mutants as stress-mimic models. 2010. *Journal of Experimental Botany* 61: 4197-4220.

Rowley, J. R., and J. S. Rowley. 1983. Modification of the exine during germination of pollen grains of *Ulmus*. In *Pollen: Biology and Implications for Plant Breeding*. eds. D. L. Mulcahy and E. Ottaviano. Elsevier. 173-182.

Scott, R. J. 1994. Pollen exine: the sporopollenin enigma and the physics of pattern. In *Molecular and Cellular Aspects of Plant Reproduction* eds. R. J. Scott and A. D. Stead. Cambridge University Press. 49-80.

Seymour, R. S., and A. J. Blaylock. 2000. Stigma peroxidase activity in association with thermogenesis in *Nelumbo nucifera*. *Aquatic Botany* 67: 155-159.

Smirnova, A. V., Matveyeva, N. P. and I. P. Yermakov. 2014. Reactive oxygen species are involved in regulation of pollen wall cytomechanics. *Plant Biology* 16: 252-257.

Southworth, D. 1974. Solubility of Pollen Exines. *American Journal of Botany* 61: 36-44.

Speranza, A., R. Crinelli, V. Scoccianti, and A. Geitmann. 2012. Reactive oxygen species are involved in pollen tube initiation in kiwifruit. *Plant Biology* 14: 64-76.

Swanson, R., Clark, T. and D. Preuss. 2005. Expression profiling of *Arabidopsis* stigma tissue identifies stigma-specific genes. *Sexual Plant Reproduction*. 18: 163-171.

Weston, R. J. 2000. The contribution of catalase and other natural products to the antibacterial activity of honey: a review *Food Chemistry* 71: 235-239.

Wille, J. J. and M. A. Berhow. 2011. Bioactives derived from ripe corn tassels: a possible new natural skin whitener, 4-Hydroxy-1-Oxindole-3-Acetic Acid. *Current Bioactive Compounds* 7: 126-134.

Wolters-Arts, M., Lush, W. M., and C. Mariani. 1998. Lipids are required for directional pollen-tube growth. *Nature* 392: 818-821.

Wudick, M. W. and J. A. Feijo. 2014. At the intersection: Merging Ca2+ and ROS signaling pathways in pollen. *Molecular Plant* 7: 1595-1597.

Zechmann, B., Koffler, B. E., and S. D. Russell. 2011. Glutathione synthesis is essential for pollen germination in vitro. *BMC Plant Biology* 11:54.

Zinkl G. M., Zwiebel B I Grier D G., and D. Preuss. 1999. Pollen-stigma adhesion in *Arabidopsis*: a species-specific interaction mediated by lipophilic molecules in the pollen exine. *Development* 126: 5431-40.

What is claimed is:

1. A coating composition comprising a sporopollenin-based matrix and a resin based carrier suitable for forming an inert coating onto a surface, wherein the sporopollenin is admixed with said carrier in a ratio of between 10:1 to 1:10 carrier to sporopollenin, wherein said coating composition is suitable to create a selectively inert barrier when applied to said surface, wherein the carrier is selected from the group consisting of an epoxy, polyurethane, acrylic, alkylic, polyester resins, and combinations thereof.

2. The composition of claim 1, wherein the matrix is at least 2 pollen grains thick.

3. The composition of claim 1, wherein said carrier is a solid, non-solid, or liquid at room temperature.

4. The composition of claim 3, wherein said liquid carrier can be applied to said surface in liquid form.

5. The composition of claim 3, wherein said non-solid carrier can be applied to said surface by rolling the non-solid carrier onto the surface.

6. The composition of claim 1, wherein the carrier is cured by application of a solvent or catalyst.

7. The composition of claim 1, wherein the surface is metallic.

8. The composition of claim 1, further comprising a crosslinking agent.

9. The composition of claim 8, wherein the crosslinking agent is selected from the group selected from: aliphatic or aromatic primary or secondary amines, tertiary amines, boron trihalides and salts thereof, organic acid salts; di and poly anhydrides, di and poly phenols, imidazoles, and combinations thereof.

10. The composition of claim 1, wherein the carrier is heat cured.

11. The composition of claim 1, wherein the carrier is not degraded by a strong acid.

12. The composition of claim 1, wherein the carrier is selectively degradable by a composition comprising a peroxidase, a catalase, and a peroxide.

* * * * *

UNITED STATES PATENT AND TRADEMARK OFFICE
CERTIFICATE OF CORRECTION

PATENT NO. : 10,913,937 B2
APPLICATION NO. : 15/955416
DATED : February 9, 2021
INVENTOR(S) : Anna F. Edlund Page 1 of 1

It is certified that error appears in the above-identified patent and that said Letters Patent is hereby corrected as shown below:

In the Specification

Column 1, Lines 11-13, replace "This invention was made with govern n support under Grant RUI#0744943 to A. F. E awarded by the National Science Foundation." with --This invention was made with government support under Grant No. 1138371 awarded by the National Science Foundation.--

Signed and Sealed this
Third Day of May, 2022

Katherine Kelly Vidal
*Director of the United States Patent and Trademark Office*